(12) United States Patent
Theobald

(10) Patent No.: US 9,833,228 B2
(45) Date of Patent: Dec. 5, 2017

(54) SUTURE AND ANCHOR ENGAGEMENT METHODS AND RESULTING DEVICES

(71) Applicant: Cook Medical Technologies LLC, Bloomington, IN (US)

(72) Inventor: Elizabeth A. Theobald, Bloomington, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 318 days.

(21) Appl. No.: 13/746,408

(22) Filed: Jan. 22, 2013

(65) Prior Publication Data

US 2013/0190816 A1 Jul. 25, 2013

Related U.S. Application Data

(60) Provisional application No. 61/590,049, filed on Jan. 24, 2012.

(51) Int. Cl.
*A61B 17/04* (2006.01)
*A61B 17/06* (2006.01)
*A61B 17/00* (2006.01)

(52) U.S. Cl.
CPC .......... *A61B 17/0401* (2013.01); *A61B 17/06* (2013.01); *A61B 2017/00526* (2013.01); *A61B 2017/0409* (2013.01); *A61B 2017/0417* (2013.01)

(58) Field of Classification Search
CPC ................ A61B 17/0401; A61B 17/06; A61B 2017/00526; A61B 2017/0409; A61B 2017/0417
See application file for complete search history.

(56) References Cited

U.S. PATENT DOCUMENTS

| 3,513,848 | A | * | 5/1970 | Garvey et al. ................. 606/228 |
| 4,968,315 | A | | 11/1990 | Gatturna |
| 5,041,129 | A | | 8/1991 | Hayhurst et al. |
| 5,084,063 | A | * | 1/1992 | Korthoff .......... A61B 17/06004 606/226 |
| 5,123,914 | A | * | 6/1992 | Cope .................. A61B 17/0401 606/108 |
| 5,269,809 | A | * | 12/1993 | Hayhurst ........... A61B 17/0401 606/151 |
| 5,374,278 | A | | 12/1994 | Chesterfield et al. |

(Continued)

OTHER PUBLICATIONS

Datta, Arindam et al., "The Effects of Annealing Conditions on the Structure and Properties of Polypropylene Fibers," Medical Plastics and Biomaterials Magazine, http://www.deviceink.com/mpb/archinve/97/11/005.html last printed Mar. 20, 2010.

(Continued)

*Primary Examiner* — Tuan V Nguyen
(74) *Attorney, Agent, or Firm* — Woodard, Emhardt, Moriarty, McNett & Henry, LLP

(57) ABSTRACT

Described are methods and systems for engaging sutures and anchors and the resulting suture and anchor sets. In certain aspects, an end of the suture may be heated to create a melted mass of suture material. The melted mass may act as a shoulder to resist backing out of a hole in the anchor through which the suture is threaded, thereby engaging the suture and the anchor. Adhesive material may optionally be used to enhance the engagement between the suture and anchor.

15 Claims, 6 Drawing Sheets

(56) References Cited

U.S. PATENT DOCUMENTS

| | | | |
|---|---|---|---|
| 5,417,691 A * | 5/1995 | Hayhurst | A61B 17/0401 606/139 |
| 5,665,111 A | 9/1997 | Ray et al. | |
| 5,702,352 A * | 12/1997 | Kimura et al. | 600/201 |
| 5,964,783 A * | 10/1999 | Grafton et al. | 606/232 |
| 6,488,690 B1 | 12/2002 | Morris et al. | |
| 6,626,919 B1 * | 9/2003 | Swanstrom | A61B 17/0643 606/153 |
| 6,866,672 B2 | 3/2005 | Mollenauer et al. | |
| 2001/0002439 A1 * | 5/2001 | Bonutti | A61B 17/0401 606/232 |
| 2008/0033232 A1 * | 2/2008 | Catanese et al. | 600/29 |
| 2008/0086152 A1 | 4/2008 | McKay et al. | |
| 2011/0106155 A1 * | 5/2011 | Theobald | A61B 17/0487 606/232 |
| 2013/0204295 A1 * | 8/2013 | Hunter | A61B 17/0401 606/228 |

OTHER PUBLICATIONS

Internet pages, "The Manufacturing Process," How suture is made—material, manufacture, making, history etc., http://www.madehow.com/Volume-7/Suture.html last printed Mar. 30, 2010.

* cited by examiner

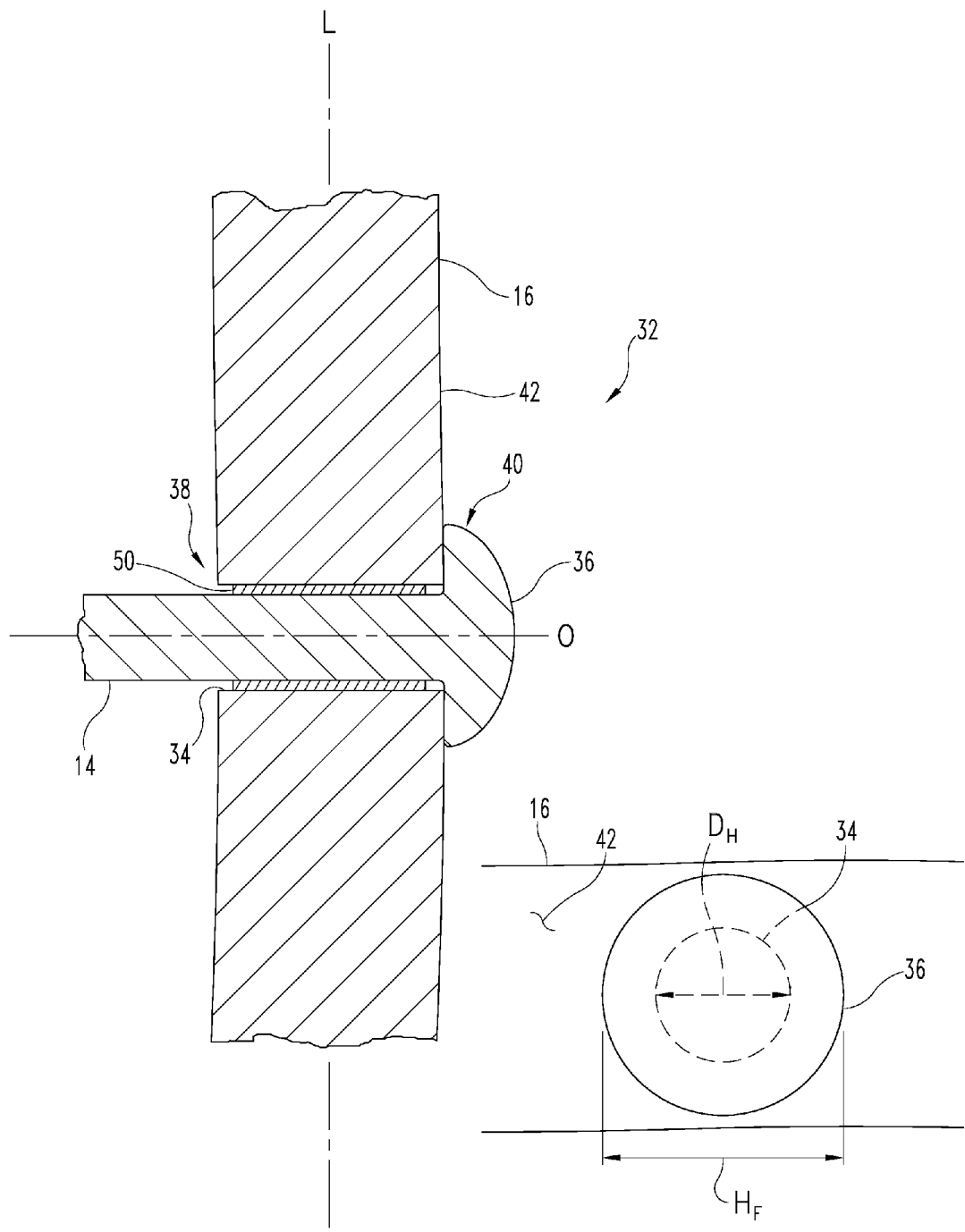
*Fig. 2*  *Fig. 3*

SUTURE AND ANCHOR ENGAGEMENT METHODS AND RESULTING DEVICES

CROSS-REFERENCE TO RELATED APPLICATIONS

This application claims the benefit of U.S. Provisional Application No. 61/590,049 filed Jan. 24, 2012, which is hereby incorporated by reference.

BACKGROUND

The present disclosure relates generally to medical technology and in particular aspects to methods and systems for engaging sutures and anchors and combination suture and anchor devices that can be made thereby. As further background, there exist a variety of medical procedures in which secure suture and anchor sets are necessary to secure patient tissue before, during and/or after the procedure. Many types of medical procedures utilize suture and anchor sets to secure tissue in place while catheters or other devices are inserted into the body. Insertion of such devices often relies, in part, on the successful anchoring of the surrounding tissue, and thus on the integrity of the suture and anchor set.

Several methods have been suggested for engaging sutures and anchors, including various methods of tying the suture to the anchor. Such engagement methods rely on the strength of the tied arrangement; however, such arrangements can fray, loosen, come untied, unravel or otherwise lose strength and integrity over time or upon the application of force along the suture and anchor set. Additionally, such tied arrangements can unnecessarily occupy space about the anchor and/or present knotted surface structures, making deployment and/or placement of the suture and anchor set difficult.

There remain needs for improved and/or alternative systems and methods for engaging sutures and anchors. The present disclosure is addressed to those needs.

SUMMARY

The present disclosure provides, in certain aspects, unique methods and systems for securely engaging sutures and anchors. In certain embodiments, the present disclosure provides unique methods and systems for securely engaging sutures and anchors without the need for knots, as by employing melt-deformed masses of suture material that contribute to securement of a suture to an anchor.

In one embodiment, an anchor is provided for securing a strand of suture material in the body. The particular anchor defines a passageway through which a suture is threaded. The distal end of the suture includes an integral polymeric mass as a shoulder configured to prevent the distal end of the suture from passing through the passageway, thereby disengaging the suture and the anchor. To form the shoulder, the distal end of the suture may be heated causing the suture to melt at its distal end.

In another embodiment, a suture is engaged with an anchor via a melted end flange at the distal tip of the suture. The suture is threaded through a hole in the anchor and the melted end flange is configured to prevent the suture from passing through the hole to disengage the components. The melted end flange is of a low profile such that the engaged anchor and suture are able to advance through the central lumen of a delivery needle for deployment at a location within the patient's body.

In yet other embodiments, adhesive may optionally be used to assist in the engagement between a suture and an anchor, in addition to the engagement methods discussed herein.

Other objects, embodiments, forms, features, advantages, aspects, and benefits of the present disclosure shall become apparent from the detailed description and drawings included herein.

BRIEF DESCRIPTION OF THE DRAWINGS

FIG. 2 is a partial, cross-sectional view of the medical system of FIG. 1.

FIG. 3 is a partial, side view of an inventive medical system according to another embodiment of the present disclosure.

DETAILED DESCRIPTION

Figure 1:
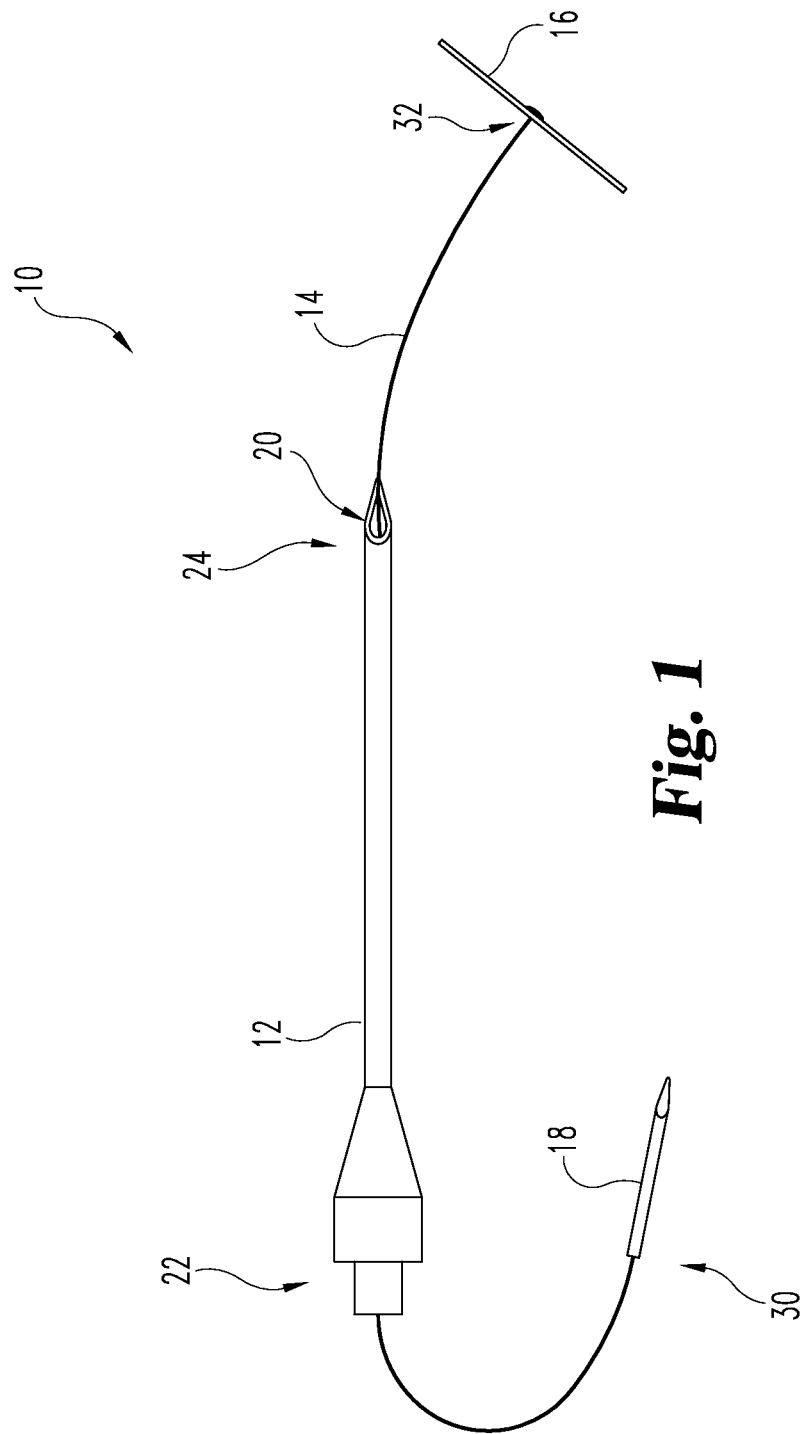
FIG. 1 is a partial view of an inventive medical system according to an embodiment of the present disclosure.

While the present disclosure may be embodied in many different forms, for the purpose of promoting an understanding of the principles of the present disclosure, reference will now be made to the embodiments illustrated in the drawings, and specific language will be used to describe the same. It will nevertheless be understood that no limitation of the scope of the claims is thereby intended. Any alterations and further modifications in the described embodiments and any further applications of the principles of the present disclosure as described herein are contemplated as would normally occur to one skilled in the art to which the disclosure relates.

In certain aspects, the present disclosure provides unique methods and systems for engaging sutures and anchors and the resulting unique suture anchor sets, for use in a variety of medical procedures. The present disclosure provides for secure engagement of sutures and anchors, and in certain inventive embodiments, secure engagement of sutures and anchors without the use of knots, fasteners or other similar engagement methods and/or devices. Additionally, in certain inventive embodiments, the present disclosure provides securely engaged suture and anchor sets having a relatively slender or low profile. To securely engage a suture and an anchor according to the present disclosure, an end of the suture may be heated to create an integral melted mass on the suture tip, the melted mass being configured to prevent the suture from backing out of a hole in the anchor through which the suture is threaded. In certain optional embodiments, adhesive may also be used to assist in securing the suture and anchor together.

With reference now to FIG. 1, shown is a suturing and anchoring system 10 according to a particular embodiment.

In this illustrative arrangement, a suture 14 is coupled to an anchor 16 at one end and an optional suture needle 18 at the other end. An example introducer needle 12 may be used to introduce, deploy and/or secure the illustrated suture 14 and anchor 16 in the body. In doing so, the suture and anchor set is inserted into central lumen 20 of needle 12 through proximal end 22, travels through central lumen 20, and is deployed out distal end 24 at a location in the body. A variety of other suitable delivery instruments may be used in this regard.

FIG. 2 illustrates a particular version of the inventive engagement between suture 14 and anchor 16. Suture 14 may be threaded through a hole 34 defined in anchor 16 and include a melt-deformed integral polymeric mass, such as the illustrated flange or shoulder 36, at its distal tip 32. As shown, hole 34 extends along an opening axis O that is non-parallel (e.g. perpendicular in the illustrated embodiment) to a longitudinal axis L of anchor 16. The shoulder 36 is preferably resistant to passage through hole 34. In this way, shoulder 36 may be configured to prevent the suture 14 from exiting or backing out of hole 34. In the particular illustrated embodiment, hole 34 includes a proximal end opening 38 and a distal end opening 40, with the shoulder 36 positioned adjacent distal end opening 40 so as to prevent the distal tip 32 of suture 14 from passing through opening 40 and hole 34, thus disengaging suture 14 from anchor 16 and losing integrity of the suture and anchor set. As discussed in greater detail below, adhesive may also optionally be used to assist in securing the suture and anchor, with one non-limiting example being the illustrated adhesive 50 positioned in hole 34.

Shoulder 36 may extend beyond the perimeter of hole 34 alongside outer wall 42 of anchor 16 at least one point along the perimeter of the hole, and in certain particular embodiments, extends beyond hole 34 at all points around the perimeter of the hole. The periphery of shoulder 36 preferably extends beyond hole 34 a sufficient distance to allow for adequate resistant contact between shoulder 36 and wall 42 to prevent suture and anchor disengagement.

Figures 4, 5:
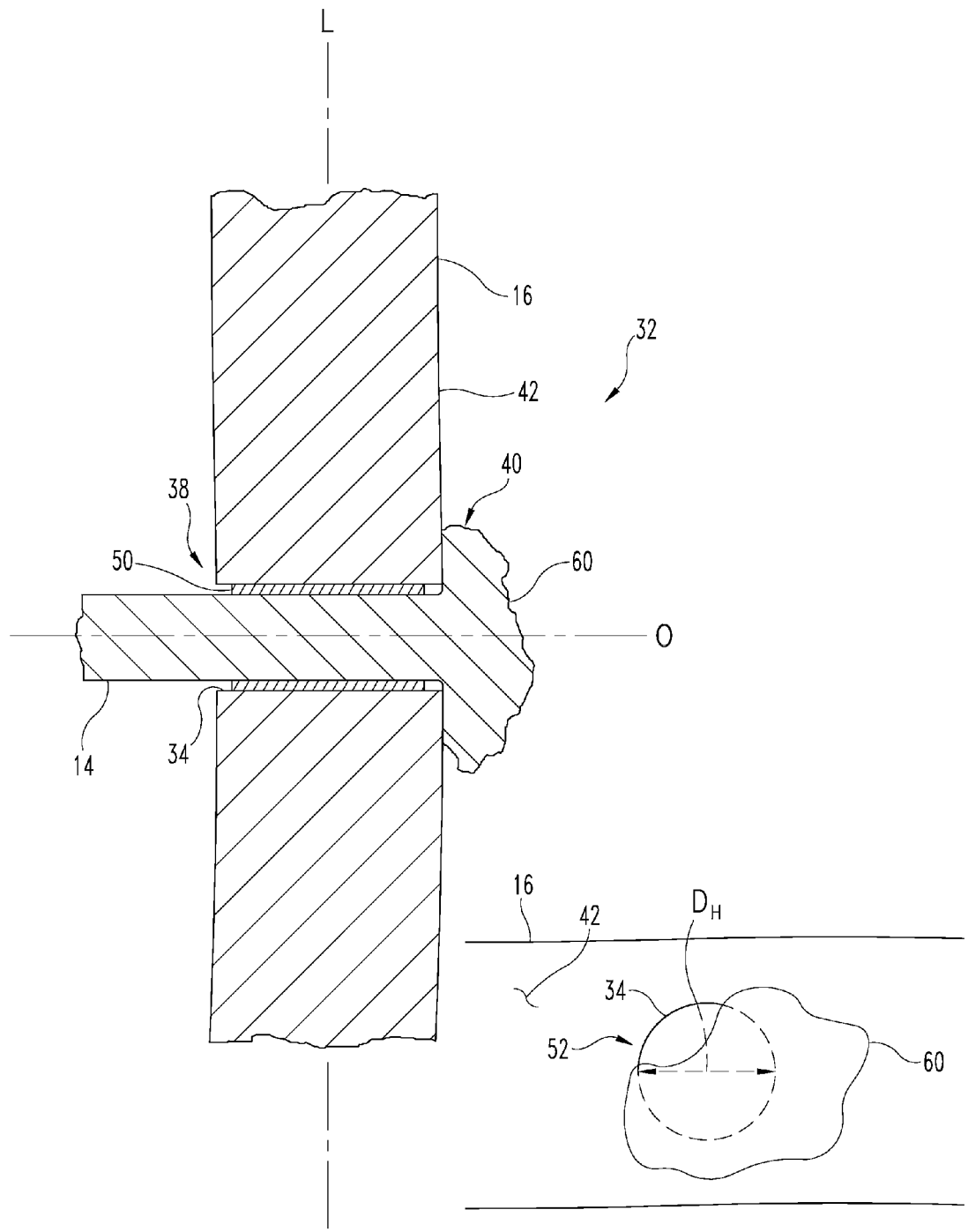
FIG. 4 is a partial, cross-sectional view of an inventive medical system according to another embodiment of the present disclosure.
FIG. 5 is a partial, side view of the medical system of FIG. 4.
Figure 6:
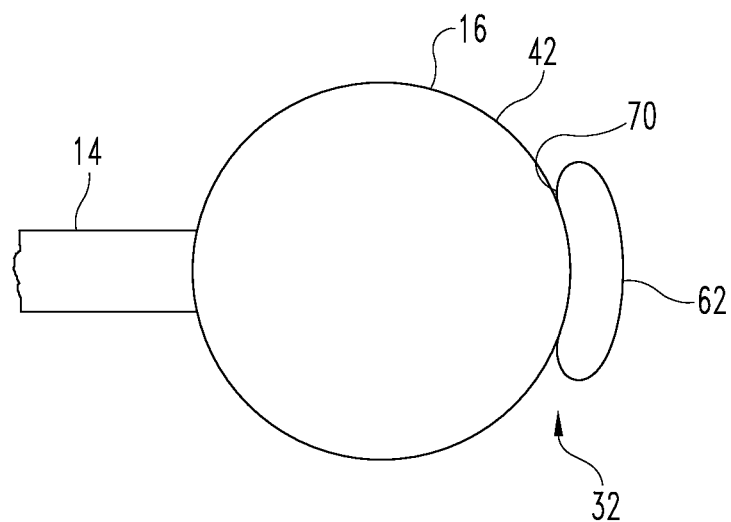
FIG. 6 is a partial, end view of an inventive medical system according to another embodiment of the present disclosure.

The melt-deformed integral polymeric mass (e.g. shoulder or flange 36) is necessarily sized and configured such that it cannot pass through hole 34, so as to maintain the engagement of suture 14 and anchor 16. Although the particular illustrated shoulder 36 is shown as having a substantially regular shape, FIGS. 5 and 6 illustrate an example of a shoulder 60 having an irregular shape which may be typical of the melt-deformed mass. The melted mass created at the distal tip of the suture may assume a variety of other appropriate shapes and configurations, in addition to those of shoulder 36 and shoulder 60 as two non-limiting examples. For instance, other random or irregular shapes and configurations could be used, such that the distal tip 32 is prevented from passing through hole 34.

The illustrated shoulder 36 assumes a substantially circular shape in the plane shown in FIG. 3. In this particular configuration, the width or height $H_F$ of flange or shoulder 36 may also be the diameter of shoulder 36 which, as shown, is larger than the diameter $D_H$ of hole 34, both diameters being taken perpendicular to opening axis O of hole 34. The dimension $D_H$ shown in FIG. 3 is taken along surface 42, e.g. substantially along a longitudinal axis of a cylindrical anchor 16. Accordingly, shoulder 36 is sized such that it is not capable of passing through hole 34.

FIG. 4 shows a cross-sectional view of the illustrated example shoulder 60. The illustrated shoulder 60 assumes an irregular shape and, as shown in FIG. 5, only partly extends beyond hole 34, such that a portion 52 of hole 34 is left uncovered by the shoulder 60. Despite the partial covering of hole 34, sufficient resistant contact is made between shoulder 60 and outer wall 42 to inhibit removal of suture 14 through hole 34 of anchor 16. As seen in the figures, in some embodiments a sufficient resistant contact can be made where the area of contact between shoulder 60 and wall 42 is at least approximately the same as the area of hole 34 at wall 42.

Figure 7:
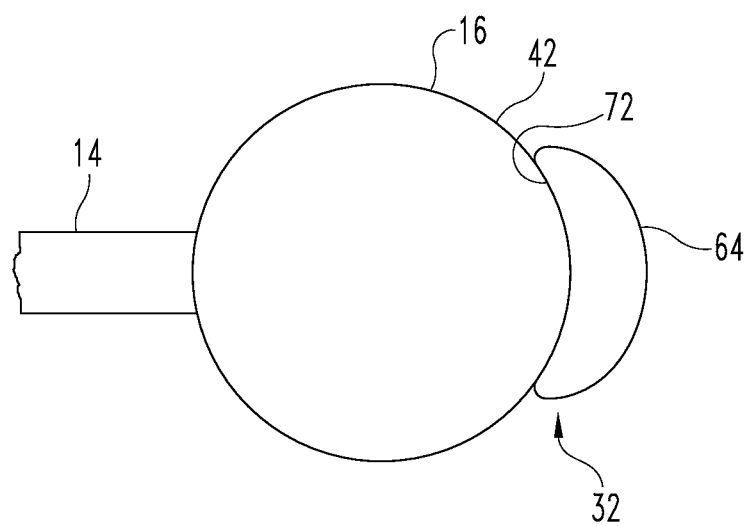
FIG. 7 is a partial, end view of an inventive medical system according to another embodiment of the present disclosure.

FIGS. 6 and 7 illustrate two examples of the numerous possible shapes that the melted shoulder may assume with respect to the plane shown in those figures. As illustrated, the melted flange or shoulder may assume an elliptical shape (such as shoulder 62 in FIG. 6) or a crescent shape (such as shoulder 64 in FIG. 7), as non-limiting examples. When considering three dimensions, the melted flange or shoulder may assume a variety of appropriate shapes, including the shape of a variety of ellipsoids, such as discal and spheroidal shapes as non-limiting examples.

Example shoulder 62 shown in FIG. 6 includes an underside surface 70, and example shoulder 64 shown in FIG. 7 includes an underside surface 72. As evident from a comparison of FIGS. 6 and 7, the underside surfaces of the shoulders contemplated by the present disclosure may contact outer wall 42 of anchor 16 in varying amounts depending on the shape of the shoulder. In the particular illustrated examples, underside surface 70 is in partial contact with outer wall 42, while underside surface 72 is in substantially complete contact with outer wall 42. The exact amount of contact between the underside surface of the melted shoulder and the outer wall 42 can vary, so long as the melted shoulder is sized and configured such that it is capable of preventing the distal tip 32 of suture 14 from passing through hole 34, thereby disengaging the suture and the anchor.

Figure 8:
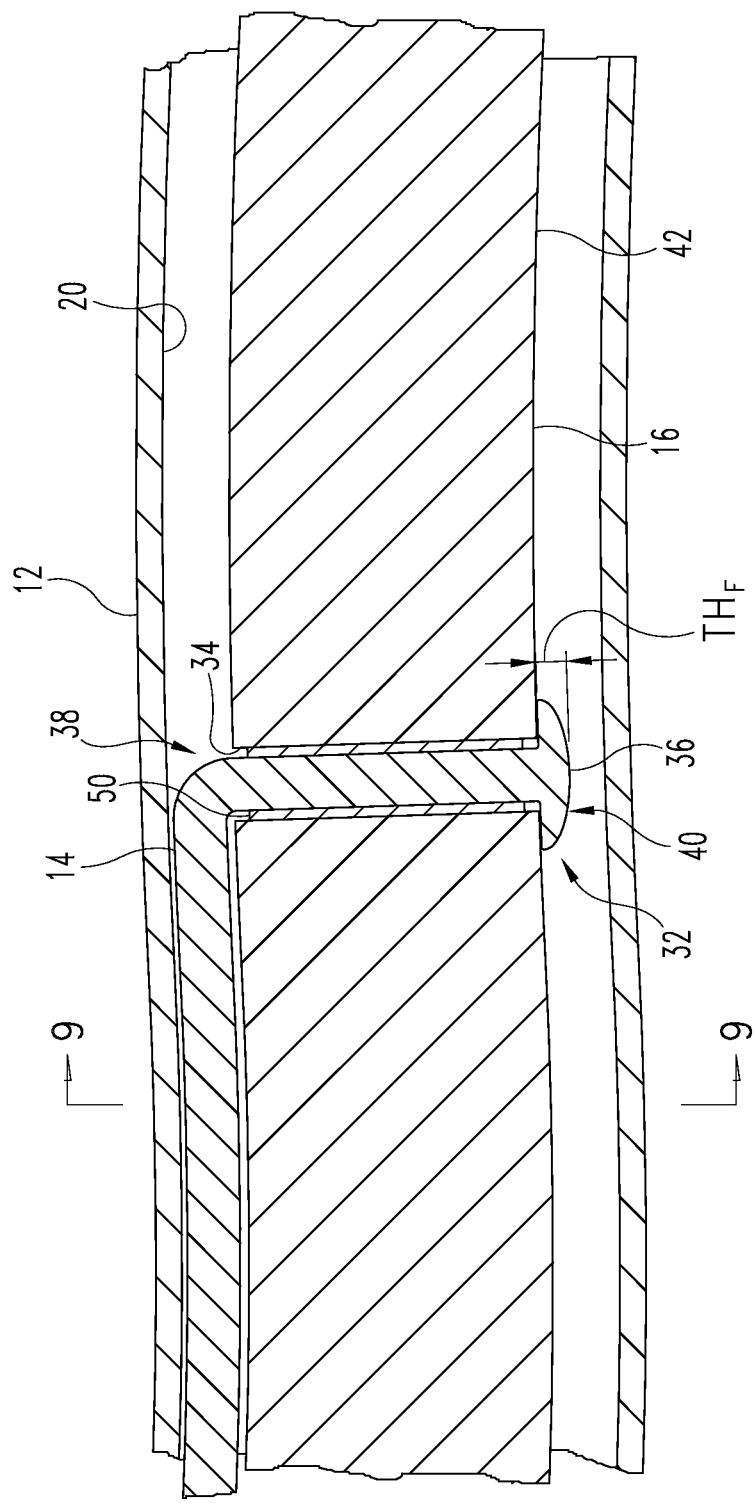
FIG. 8 is a partial, cross-sectional view of the medical system of FIG. 1.
Figure 9:
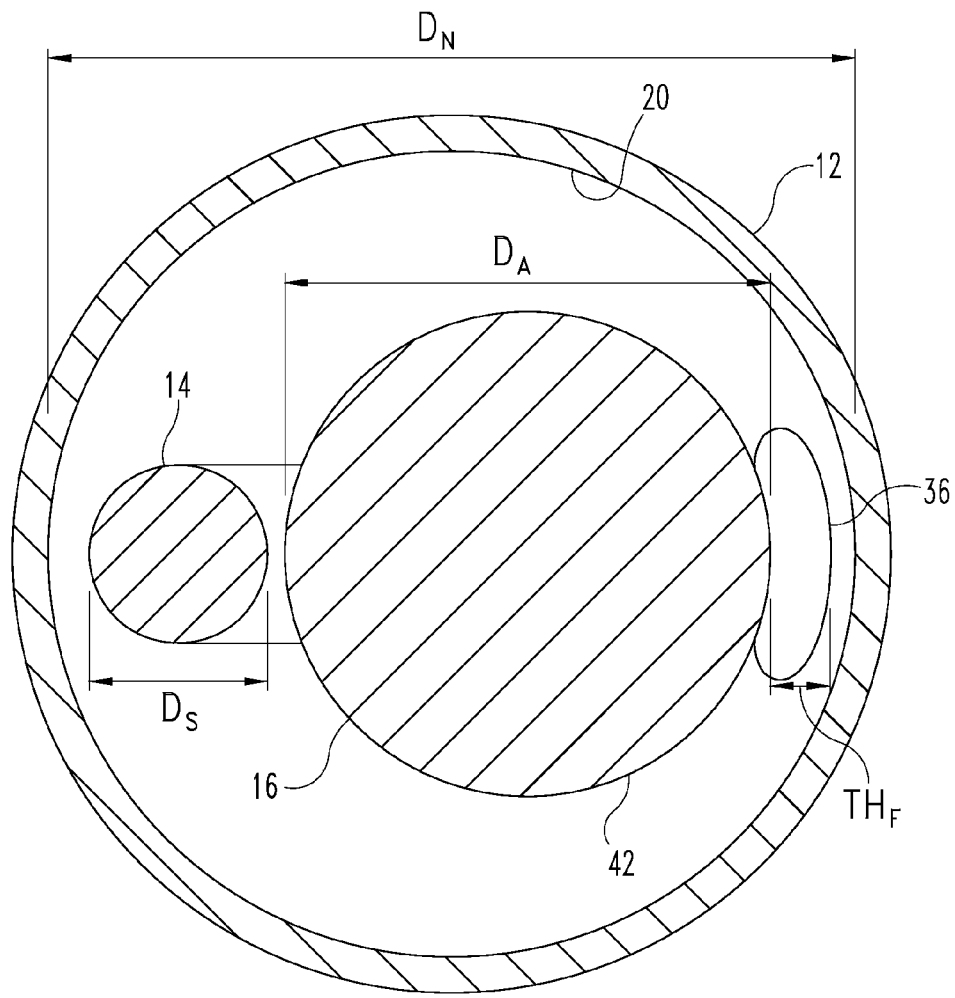
FIG. 9 is a cross-sectional view of the medical system of FIG. 8 taken along section line 9-9.

In certain inventive embodiments, the melted flange or shoulder contemplated by the present disclosure (such as shoulder 36 for example) assumes a relatively slender or low profile to enable passage of the suture 14 and anchor 16 set through central lumen 20 of introducer needle 12 for deployment at a location in the body. As shown in FIG. 8, anchor 16 and suture 14 having shoulder 36 must necessarily be sized and configured to allow for travel within the central lumen 20. In typical procedures, as anchor 16 is advanced through central lumen 20, suture 14 may fold alongside the outer wall 42 of anchor 16 opposite from shoulder 36, as illustrated in FIG. 8. Accordingly, in certain embodiments the inner diameter $D_N$ of introducer needle 12 (or the diameter of central lumen 20) must be larger than the combination of diameter $D_S$ of suture 14, diameter $D_A$ of anchor 16, and largest thickness $TH_F$ of flange or shoulder 36, as shown in FIG. 9. For the purposes of the present disclosure, the thickness $TH_F$ of shoulder 36 is the greatest distance that shoulder 36 extends beyond outer wall 42 of anchor 16.

The following is one particular non-limiting example to illustrate the low-profile configuration of the melted flange or shoulder contemplated by the present disclosure. Assuming introducer needle 12 is a 17 gage needle having an inner diameter $D_N$ of around 0.050 inches, anchor 16 has a $D_A$ of around 0.038 inches, and suture 14 has a diameter $D_S$ of around 0.008 inches, a clearance distance of around 0.004 inches remains for passage of shoulder 36. Accordingly, in this particular example, the thickness $TH_F$ of shoulder 36 must be less than 0.004 inches.

In the above example embodiment, a thickness $TH_F$ of less than 0.004 inches results in the thickness $TH_F$ of shoulder 36 occupying less than 8% of the diameter $D_N$ of introducer needle 12. To that end, in this particular example, the outermost surface of shoulder 36 extends beyond the anchor 16 at a farthest point (shown as thickness $TH_F$) a distance equal to about 10.5% of the diameter $D_A$ of anchor 16. In certain preferred embodiments, the thickness $TH_F$ of shoulder 36 extends beyond anchor 16 a distance less than 15% of the diameter $D_A$ of anchor 16. In certain other preferred embodiments, the thickness $TH_F$ of shoulder 36 extends beyond anchor 16 a distance less than 10% of the diameter $D_A$ of anchor 16. It should be appreciated that the present disclosure contemplates that the shoulder 36 may be sized differently with respect to anchor 16 and the inner diameter of the needle utilized to introduce suture 14 and anchor 16 into the body. It should be understood that larger or smaller values for the dimensions discussed herein could be used in accordance with this disclosure.

In alternative embodiments, the melt-deformed integral polymeric mass may be positioned within the hole or passageway defined in the anchor, with the mass being sized and configured to prevent the suture from exiting or backing out of the hole. In some embodiments, part or all of the mass may be lodged within the hole, or otherwise engaged via interference fit, such that the mass is substantially non-moveable within the hole. In other embodiments, the mass may be movable within a portion of the hole, yet prevented from exiting or backing out of another portion of the hole. In certain embodiments, the hole may include a changing diameter such that the mass is resistant to passage through a portion of the hole as the hole's diameter decreases.

In the illustrated example, anchor 16 is shown as cylindrical in shape with a length along a longitudinal axis L and a constant circular cross-sectional diameter. While the illustrated anchor is cylindrical, such anchoring members when utilized in the present disclosure can be shaped and configured in a variety of other appropriate ways. These include various shaped three-dimensional constructs, and even some sheet-like or generally two-dimensional implantable members. When an anchoring member relies, at least in part, on its size and shape to perform its anchoring function, this sort of member can be shaped and configured in a variety of manners. To that end, a variety of different sized introducer needles, sutures and/or other components discussed herein may be used in accordance with the principles of the present disclosure.

An example method of engagement of suture 14 and anchor 16 will be discussed with general reference to FIGS. 1-9. As one component of the engagement, suture 14 is passed through a pre-formed passageway in the anchor, such as hole 34 in anchor 16. Suture 14 may be threaded through hole 34 in a variety of appropriate, known techniques which are not critical. In alternative embodiments, suture 14 may be threaded or otherwise passed through anchor 16 in the absence of a pre-formed passageway. To accomplish this, the suture may be engaged with a needle configured to advance the suture through the anchor and necessarily create a passageway as the suture is threaded.

The present disclosure contemplates that the distal tip 32 of suture 14 may be heated to create the melted mass, such as the illustrated shoulders 36, 60, 62 and/or 64 for example, either before or after suture 14 is passed through the anchor. It is contemplated that, in some applications, heating the suture tip 32 after passing the suture 14 through hole 34 causes the melted shoulder to at least partially conform to the shape of outer wall 42 of anchor 16. Shoulder 64 shown in FIG. 7 is one example of such a result. In some embodiments, a portion of the melted mass may adhere to an area along the outer wall 42 as a result of the heating of the suture tip 32, enhancing the engagement between suture 14 and anchor 16.

The melted mass (such as the illustrated shoulders 36, 60, 62 and/or 64) may be created by heating the distal tip 32 of suture 14 via a variety of appropriate heating techniques. It is contemplated that the distal tip 32 is heated to a sufficient degree to cause melting of the material comprising suture 14. Various manners of heating distal tip 32 can be used, such as by contact heating (e.g. by a hot iron) or application of radiant energy, or by combinations of heating steps.

Heating the distal tip 32 of suture 14 causes one or more characteristics of the suture material to change or transition. In embodiments in which suture 14 is composed of a polymeric material, the heating process causes the polymeric fibers of the distal tip to transition from a more crystalline-like structure to a more amorphous-like structure. As a result, the melt-deformed integral polymeric mass may assume a more amorphous state than the remainder of the suture material.

As mentioned above in connection with FIG. 2, an adhesive 50 may optionally be applied within hole 34 to further secure the engagement between suture 14 and anchor 16. In this way, while shoulder 36 may prevent distal tip 32 from passing through hole 34, adhesive 50 functions to assist by gripping a portion of suture 14 in hole 34 and/or to prevent proximal end 30 from passing through hole 34. The present disclosure contemplates that adhesive may be applied at other locations to assist in securing the engagement either in addition to or in lieu of adhesive within hole 34. As an example, adhesive may be applied to the underside surface of the melted mass to adhere the melted mass to the outer wall 42 of anchor 16. The adhesive optionally used as part of the present disclosure may be any type of appropriate adhesive which is considered safe for biological applications, such as cyanoacrylates for example. In some embodiments, adhesive is absent from the suture and anchor set.

It is preferred, but not necessary, that the engagement of suture 14 and anchor 16 occur prior to deployment in the body, so that suture and anchor set may be quickly and easily implanted. Accordingly, upon engagement of the suture 14 and anchor 16, the suture and anchor set (with or without the inclusion of suture needle 18), may be advanced through introducer needle 12 through a variety of known techniques and deployed at a location in the body. The suture and anchor sets according to the present disclosure may be utilized in a variety of medical applications to secure tissue in the body. To give one particular example of how the suture and anchor sets may be used, one or more sets may be employed to secure the patient's stomach to the abdominal or peritoneal wall to allow for insertion and placement of a catheter or other medical device into the patient's stomach. However, it should be appreciated that the suture and anchor sets contemplated by the present disclosure may be utilized in a variety of other medical applications.

Suture 14 and anchor 16 may be formed with a variety of biocompatible materials. In certain preferred embodiments, suture 14 and/or anchor 16 may be composed of bioresorbable, bioabsorbable or biodegradable materials. Examples of certain bioresorbable, bioabsorbable or biodegradable polymers that may be used to form suture 14 and/or anchor 16 include, but are not limited to, poly(L-lactic acid), polycaprolactone, poly(lactide-co-glycolide), poly(hydroxybutyrate), poly(hydroxybutyrate-co-valerate), polydioxanone, polyorthoester, polyanhydride, poly(glycolic acid), poly(D, L-lactic acid), poly(glycolic acid-co-trimethylene carbonate), polyhydroxyalkanaates, polyphosphoester, polyphosphoester urethane, poly(amino acids), cyanoacrylates, poly(trimethylene carbonate), poly(iminocarbonate), copoly(ether-esters) (e.g., PEO/PLA), polyalkylene oxalates, and polyphosphazenes.

Regarding suture 14, while suture material in particular will be useful in certain inventive embodiments, a variety of other elongate materials and objects capable of being anchored can be used as an alternative to, or in addition, to suture material. These include various types of cords, filaments, chains, strings, wires and other similar objects having relatively slender profiles for extending through patient tissue. Additionally, regarding anchor 16, any suitable anchoring device or adaptation may be utilized in this regard to secure the suture in place. Some of these devices will be designed to penetrate into surrounding tissues and other will not. In some instances, in addition to providing an anchoring function at a treatment site, an anchoring member will serve one or more additional functions there.

The combination suture and anchor devices or systems contemplated by the present disclosure may be used in a variety of medical procedures in which it is desirable to anchor tissue. As part of certain medical procedures, it may be desirable to secure tissue to allow for the placement of a catheter. As particular examples, one or more suture and anchor combinations may be used to secure a patient's stomach to the abdominal wall or the peritoneum to allow for the placement of a catheter into the patient's stomach and/or small intestine, such as a gastrostomy or gastrojejunostomy catheters. It is contemplated that the suture and anchor combinations contemplated by the present disclosure may be utilized as part of various other medical procedures as would occur to one of ordinary skill in the art.

Any or all of the components described herein can be provided in a sterile pack for providing necessary parts, or a variety of parts, to a surgeon. For example, one or more predetermined types or sizes of introducer needle and engaged suture, anchor and/or suturing needle may be provided in a single sterile package or kit. A surgeon can choose the sizes or types of components he or she wishes to use during surgery. Alternatively, sterile kits containing predetermined sizes or types of components may be provided. Packages or kits of the components described herein can include additional devices or tools which may be useful in the particular medical procedure being performed.

While the disclosure has been illustrated and described in detail in the drawings and foregoing description, the same is to be considered as illustrative and not restrictive in character, it being understood that only selected embodiments have been shown and described and that all equivalents, changes, and modifications that come within the spirit of the disclosure as defined herein or by the following claims are desired to be protected.

What is claimed is:

1. A suture anchor apparatus, comprising:
   an anchor for securing a strand of suture material in the body, the anchor having a first end, a second end, and an anchor body extending between the first end and second end, the anchor defining a passageway extending through the anchor body at a position intermediate to the first end and the second end of the anchor, the passageway having a distal end opening intermediate to the first end and second end of the anchor body, and the anchor body having an outer wall surface surrounding the distal end opening; and
   a suture engaged with the anchor, wherein a portion of the suture extends through the passageway, the suture having a proximal end and a distal end;
   a suture needle attached to the proximal end of the suture;
   wherein the distal end of the suture includes a melt-deformed integral polymeric mass configured to prevent the distal end of the suture from passing through the passageway thereby disengaging the suture and the anchor, the melt-deformed integral polymeric mass positioned intermediate to the first end and the second end of the anchor and abutting at least a portion of the outer wall surface surrounding the distal end opening; and
   a delivery needle having a central lumen, a leading end, and a trailing end, wherein the anchor is deployable from the leading end of the delivery needle, and wherein the suture is of sufficient length to extend through the central lumen from the leading end of the delivery needle and out of the trailing end of the delivery needle when the anchor is deployed from the leading end of the delivery needle;
   wherein the anchor is cylindrical in shape;
   wherein the integral polymeric mass has an outermost surface extending beyond said outer wall surface a distance less than 15% of a diameter of the anchor; and
   wherein the melt-deformed integral polymeric mass has a thickness that occupies less than 8% of a diameter of the central lumen of the delivery needle.

2. The apparatus of claim 1, wherein polymeric material of the melt-deformed integral polymeric mass has a more amorphous state than polymeric material of other portions of the suture.

3. The apparatus of claim 1, wherein the distal end opening has a diameter in a first plane, wherein the integral polymeric mass includes a largest periphery in a plane parallel to the first plane, the periphery being larger than the diameter of the distal end opening.

4. The apparatus of claim 1, further comprising an adhesive material occurring within the passageway between the anchor and the portion of the suture extending through the passageway to further engage the anchor and the suture, and a suture needle coupled to the proximal end of the suture.

5. The apparatus of claim 4, wherein the adhesive material is cyanoacrylate.

6. The apparatus of claim 1, wherein the suture and the anchor are made of one or more bioabsorbable materials.

7. The apparatus of claim 1, wherein the integral polymeric mass has an outer polymeric mass surface conforming to the outer wall surface surrounding the distal end opening.

8. The apparatus of claim 1, wherein the passageway extends perpendicular to a longitudinal axis of the anchor body.

9. A suture anchor system, comprising:
   an anchor for securing a strand of suture material in the body, the anchor having a first end, a second end, and an anchor body extending between the first end and second end, the anchor defining an opening extending therethrough configured to receive a strand of suture material, the opening including a proximal end opening at a position intermediate to the first end and the second end of the anchor and a distal end opening at a position intermediate to the first end and the second end of the anchor;
   a suture extending through the opening to engage the anchor, wherein a distal end of the suture extends beyond the distal end opening and includes a melted suture material end flange positioned adjacent and larger than the distal end opening, wherein the melted suture material end flange is resistant to passage through the opening, and wherein the melted suture material end flange is positioned intermediate to the first end and the second end of the anchor;
a suture needle attached to a proximal end of the suture;
a delivery needle having a central lumen, a leading end, and a trailing end, wherein the anchor is deployable from the leading end of the delivery needle, and wherein the suture is of sufficient length to extend through the central lumen from the leading end of the delivery needle and out of the trailing end of the delivery needle when the anchor is deployed from the leading end of the delivery needle;
wherein the anchor has a curved outer surface and the melted suture material end flange has a curved inner surface conforming to the curved outer surface of the anchor;
wherein the melted suture material end flange has an outermost surface extending beyond an outer wall surface of the anchor a distance less than 15% of the diameter of the anchor; and
wherein the melted suture material end flange has a thickness that occupies less than 8% of a diameter of the central lumen of the delivery needle.

10. The system of claim 9, wherein the melted suture material end flange is of a low profile such that the anchor and the suture are configured for passage through the central lumen of the delivery needle with a longitudinal axis of the anchor aligned with the longitudinal axis of the lumen, and with the melted suture material end flange occurring lateral to the anchor body within the lumen.

11. The system of claim 9, wherein the anchor is cylindrical in shape and includes a length extending along a longitudinal axis and a constant diameter.

12. The system of claim 9, further comprising adhesive material occurring within the opening between the suture and the anchor to further engage the anchor and the suture.

13. A method, comprising:
providing an anchor for securing a strand of suture material in the body, the anchor having a first end and a second end and defining a passageway, the passageway having a distal end opening intermediate to the first end and the second end of the anchor and a proximal end opening intermediate to the first end and the second end of the anchor;
providing a suture to be engaged with the anchor, the suture having a distal end and a proximal end;
heating the distal end of the suture, wherein the heating causes a portion of the suture to melt to create a melted polymeric mass having a more amorphous state than other portions of the suture, wherein during the heating, the melted polymeric mass conforms to an outer wall surface of the anchor;
threading the suture through the passageway in the anchor;
attaching a suture needle to the proximal end of the suture;
wherein the melted polymeric mass is positioned between the first end and the second end of the anchor and is resistant to passage through the passageway; and
wherein the melted polymeric mass has an outermost surface extending beyond said outer ace a distance less than 15% of a diameter of the anchor.

14. The method of claim 13, further comprising applying adhesive material between the anchor and the suture within the passageway to further engage the anchor and the suture.

15. A suture anchor system, comprising:
an anchor for securing a strand of suture material in the body, the anchor having a first end and a second end and an anchor body extending between the first end and second end;
a suture extending through the anchor, wherein a distal end of the suture extends through and beyond the anchor and includes a melt-deformed polymeric mass positioned between the first end and second end of the anchor and configured to prevent the end of the suture from passing through the anchor thereby disengaging the suture from the anchor; and
a delivery needle having a central lumen, a leading end, and a trailing end, wherein the anchor is deployable from the leading end of the delivery needle, and wherein the suture is of sufficient length to extend through the central lumen from the leading end of the delivery needle and out of the trailing end of the delivery needle when the anchor is deployed from the leading end of the delivery needle;
a suture needle attached to a proximal end of the suture;
wherein the anchor has a curved outer surface and the melt-deformed polymeric mass has a curved inner surface conforming to the curved outer surface of the anchor; and
wherein the melt-deformed polymeric mass has an outermost surface extending beyond said curved outer surface a distance less than 15% of a diameter of the anchor.

* * * * *